United States Patent
Michelson

(10) Patent No.: US 11,653,864 B2
(45) Date of Patent: May 23, 2023

(54) METHOD AND DEVICE FOR QUANTITATIVELY DETECTING THE FUSION CAPACITY IN CONJUGATE EYE MOVEMENTS

(71) Applicant: Georg Michelson, Baiersdorf (DE)

(72) Inventor: Georg Michelson, Baiersdorf (DE)

( * ) Notice: Subject to any disclaimer, the term of this patent is extended or adjusted under 35 U.S.C. 154(b) by 609 days.

(21) Appl. No.: 16/563,330

(22) Filed: Sep. 6, 2019

(65) Prior Publication Data

US 2021/0068734 A1    Mar. 11, 2021

(51) Int. Cl.
*A61B 5/16* (2006.01)
*A61B 5/00* (2006.01)

(52) U.S. Cl.
CPC ............ *A61B 5/163* (2017.08); *A61B 5/4064* (2013.01)

(58) Field of Classification Search
CPC ..... A61B 5/16–163; A61B 5/168; A61B 3/08; A61B 3/085; A61B 3/032; A61B 3/0325; A61B 3/0041; A61B 3/005; A61B 3/0058; A61B 3/0091; A61B 3/113
See application file for complete search history.

(56) References Cited

U.S. PATENT DOCUMENTS

| | | | | |
|---|---|---|---|---|
| 4,854,329 A | * | 8/1989 | Walruff | A61B 5/16 340/576 |
| 8,430,547 B2 | * | 4/2013 | Reichow | A61H 5/00 362/85 |
| 2020/0008725 A1 | * | 1/2020 | Bach | A61B 5/6801 |
| 2021/0153794 A1 | * | 5/2021 | Shudo | G09B 7/06 |

FOREIGN PATENT DOCUMENTS

EP    3287074 A1 *    2/2018 ............ A61B 5/162

OTHER PUBLICATIONS

Machine Translation of EP 3287074 (Year: 2018).*
Hasegawa, Tatsuhisa, et al. "Active linear head motion improves dynamic visual acuity in pursuing a high-speed moving object." Experimental brain research 194.4 (2009): 505-516. (Year: 2009).*
Bronstein, Adolfo M., Mitesh Patel, and Qadeer Arshad. "A brief review of the clinical anatomy of the vestibular-ocular connections—how much do we know?." Eye 29.2 (2015): 163-170. (Year: 2015).*
Micromedical Technologies, Vorteq, Pamplet. Printed Mar. 2014. (Year: 2014).*

* cited by examiner

*Primary Examiner* — David J. McCrosky
(74) *Attorney, Agent, or Firm* — Merchant & Gould P.C.

(57) ABSTRACT

A method quantitatively determines fusion capacity in conjugate eye movements of a subject. Visual stimuli are provided for stereopsis as a task for the subject, the stimuli being generated at a viewing angle relative to the primary viewing direction of the subject such that the subject must execute a movement of the viewing direction of the eyes away from the primary viewing direction. Each stimulus is presented for a period of time so that the subject perceives the respective stimulus. The subject reacts to the respective stimulus perceived thereby within a reaction time. The reaction time is determined as the duration between presentation of the relevant stimulus and the subject's motor response to the stimulus. The steps are carried out continuously with stimuli for stereopsis at varying cognitive degrees of difficulty. A series of measurements of reaction times is generated at different cognitive degrees of difficulty.

16 Claims, 9 Drawing Sheets

Figure 1:
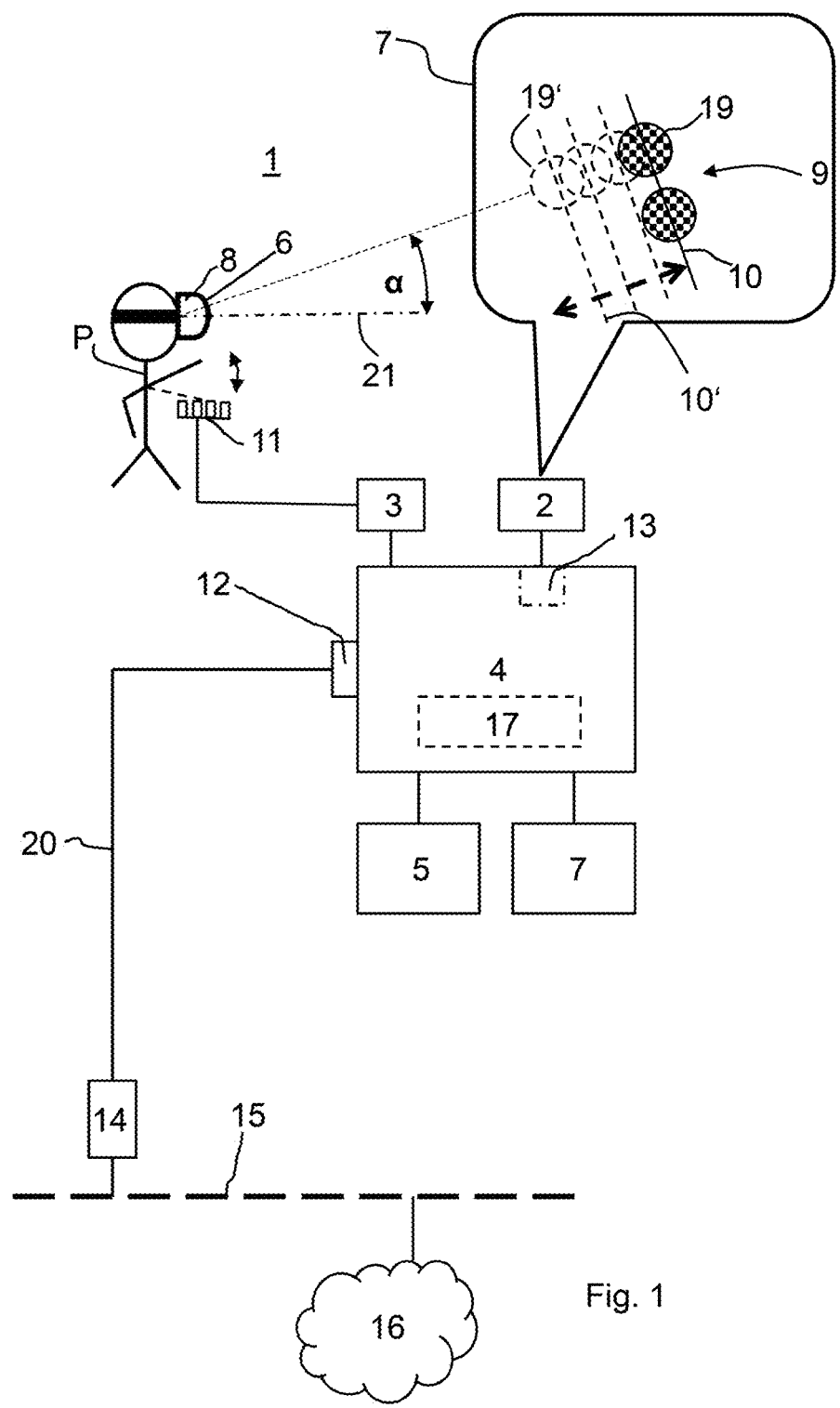

METHOD AND DEVICE FOR QUANTITATIVELY DETECTING THE FUSION CAPACITY IN CONJUGATE EYE MOVEMENTS

The present invention relates, on the one hand, to a method for quantitatively detecting the fusion capacity in conjugate eye movements and, on the other hand, to a corresponding device for carrying out the method.

TECHNOLOGICAL BACKGROUND

A concussion ("Commotio cerebri" or "Mild traumatic brain injury" or "TBI" for short) can occur after an external force impact on the head, e.g. in the event of a fall, a blow or a collision or impact. Concussion is also referred to as mild craniocerebral trauma (CCT) and is a trauma to the skull or brain. The most frequent reasons for a concussion are traffic accidents, household accidents or sports accidents. There are important indications for assuming a concussion, such as a memory gap (amnesia), head and neck pain, dizziness, nausea and vomiting and circulatory problems. The doctor usually asks the patient about the course of the accident and their complaints and assesses the severity of the concussion using a kind of checklist. Based on the patient's responses to external stimuli or verbal prompts, the physician will make an estimate of the state of consciousness. Such an examination is followed by an intensive neurological examination, which may indicate functional disorders of the nervous system. Furthermore, imaging techniques, such as computer tomography, x-rays, etc. can be used. In individual cases, measurements of the electrical brain waves can be carried out by a specialist in the electroencephalogram (EEG). In order to make a thorough diagnosis, until now it has been necessary to conduct extensive investigations over a comparatively long period of time. However, examinations using computer tomography, EEG or X-ray examinations usually only produce results when there is significant damage (tears, edema, etc.).

Recent studies have shown that the risk of developing dementia increases even after slight concussions. It is particularly worrying when people suffer from frequent brain trauma, as is the case in many sports. It is especially worrying when brain traumas are suffered in succession in a very short time, i.e. in a state in which a previously suffered brain trauma has not subsided yet. Especially in connection with risky sports, such as football, handball, rugby, boxing, etc., the risk of later dementia increases considerably for the athlete if concussions are not recognized or misinterpreted. In view of the fact that the diagnoses regarding the presence and severity of a concussion are lengthy and associated with inaccuratocies, there is a particular need for a technique that enables a rapid diagnosis.

PRINTED PRIOR ART

EP 3 287 074 B1 describes a method for detecting the cerebral cognition time of a subject, in which a visual stimulus for stereopsis is presented to a subject at different degrees of difficulty and the reaction times of the subject are recorded. From the reaction times and different degrees of difficulty, the measurements of the reaction time are adjusted by a motor reaction time component. The stimuli of varying degrees of difficulty are generated only in the primary direction of sight.

Object of the Present Invention

The object of the present invention is to provide a method and a device with which it is possible to make a systematic classification of the severity of a concussion.

Solution of the Task

According to the invention, a stimulus for stereopsis is generated at a viewing angle $\alpha$ relative to the primary viewing direction of the subject such that the subject has to perform a movement of the viewing direction of the eyes away from the primary viewing direction. The embodiment of the method according to the invention makes it possible to check the eyesight of the subject outside the primary view, i.e. in a viewing area in which the muscles controlling the eye movement are stressed or strained. In the primary viewing direction, these muscles are not needed. Especially in craniocerebral trauma, it often happens that nerves which control the muscles of the eye movements are damaged or at least impaired. For example, these are the abducens nerve, the trochlear nerve and the oculomotor nerve. Particularly in the case of disturbance of these nerves, viewing directions outside the primary area result in a disruption of the stereoscopic vision, i.e. fusion, i.e. the two images captured by the eyes no longer being correctly depicted in a single image. It has been found that by measuring the stereoscopy and the reaction speed of the subject in response to a stereopsis stimulus at a stimulus from an angle $\alpha$, a check of the condition of these nerves can be made. A check only in the primary viewing direction would provide no information in this regard, for example in a subject with a craniocerebral trauma. The determination of reaction times under stereoscopic stimuli at different degrees of difficulty (disparity difference) allows a qualitative and quantitative determination of the ability to fuse at different viewing directions. The increase in response times with increasing difficulty (i.e. decreasing disparity difference) is referred to as gain and is a measure of the visual ability to recognize stereoscopic stimuli. "Gain Controls" or "Gain of Controls" refers to the average increase in response times in msec as the difficulty of the stereoscopic stimuli increases (=decreasing disparity difference) in a healthy control group. The gain is calculated from the measured reaction time difference with respect to the difference in disparity difference. The unit of gain is [msec/arcsec].

For the first time, the method according to the invention makes it possible to obtain measurements on the basis of which, in turn, a classification of the severity of the concussion can be made. If one considers that the diagnosis of the severity of a concussion is often only possible with elaborate, lengthy and inaccurate examination methods, the method according to the invention even makes it possible to carry out rapid tests. Particularly for relevant risk groups, such as athletes or military personnel, these rapid tests make it possible immediately after a harmful event to determine whether there is a concussion and what its severity is. On this basis, it can then be decided immediately whether or not the person concerned should be prevented from engaging in a certain activity for a certain period of time. In this way, later effects, such as a very high risk of developing dementia, can be prevented effectively from the outset, or at least effectively reduced.

By setting stimuli at varying degrees of difficulty at different bent angle positions in the visual field, the fusion capacity of a subject's conjugate eye movements can be detected relative to different bent angle positions in the visual field range. Especially in craniocerebral trauma, it often happens that deficiencies in fusion capacity in conjugate eye movements show up at certain bent angle positions in the visual field, but not at other bent angle positions in the visual field. The invention thus makes it possible to quantitatively detect the ability of the conjugate eye movements to fuse relative to certain bent angle positions. In this way, measurement mapping can be done based on fusion capacity in the conjugate eye movements of a subject as a function of viewing direction.

The measured reaction times are compared with target reaction times of healthy persons. The target reaction times are empirically determined reaction times of healthy persons.

The stimulus is generated successively at different bent angles of the visual field area, the respective time of reaction to the respective stimulus of different cognitive degrees of difficulty being detected at the different bent angles.

It is useful for a plurality of bent angles $\beta$ of the visual field range to be permanently predefined in the system or its memory, the stimulus being generated at the individual bent angles $\beta$ and/or at the different degrees of difficulty of the stimulus by means of a random generator or pseudo-random generator.

The different bent angles $\beta$ preferably have a same bent angle separation to each other. As a result, the entire visual field area can be divided evenly.

The artificially generated images (stimuli) for the right eye and for the left eye differ such that with intact fusion they fuse together in the brain of the subject to form a three-dimensional image. In the stimuli for stereopsis, two or more objects can be presented which appear to subject P in different (virtual) remote optical planes relative to the subject. The presented objects can be mapped statically or dynamically. The distance between the different (virtual) remote optical planes of the objects to each other is defined by the adjustable disparity difference of the objects in the image of the right and left eye. Alternatively, stochastically generated stereo images (so-called "random dot stimuli") are used, on which certain image areas appear in another virtual image plane by a defined degree of disparity. The stereoscopic stimulus consists of at least two stereoscopically different depths of objects or areas. The degree of difficulty is determined by the disparity difference between the main virtual plane—defined by the virtual plane of objects (e.g. balls) or of random dot stimulus—and the virtual plane of the object or area on the random dot stimulus, which is stereoscopically different in depth. The stereoscopic stimulus has a virtual, spatial main plane with one or more objects and at least one object in a virtual, spatially different secondary plane. Depending on the number and location of the objects or orientations of the area on the random dot stimulus, a 2-options test or an n-options test are possible. The virtual, spatial planes of the stereoscopic objects or areas are only detectable when fusion is functional.

The task of the subject is to recognize and mark, for a given disparity difference of the two or more individual objects, that object which, due to the difference in disparity, is located in a stereoscopically different virtual plane. This object can only be recognized by the subject if there is functional fusion of the right and left eye images. With intact fusion, the subject P recognizes which object or which area appears stereoscopically closer or farther away from the virtual main plane. The subject makes this recognizable by a suitable click or a gesture on a corresponding input device such as button, pad, or controller.

In particular, the stimuli can each be an image of several objects that are fixed or rotating about their axis, one of which changes in its remote optical (also virtual) plane compared to the optical plane of the other objects depending on the disparity difference (=degree of difficulty).

Preferably, the viewing angle $\alpha$ relative to the primary viewing direction is at least 10° and a maximum of 45°. This area is particularly suitable for using a VR headset. The viewing angle $\alpha$ is preferably about 15°.

The method according to the invention makes it possible to determine the increase in the reaction time as the degree of difficulty S (gain) increases and to compare this with corresponding data of healthy persons (gain controls).

In an advantageous manner, the measurements are determined in the form of measurements of the reaction time (e.g. in msec) assigned to degrees of difficulty in arcsec (disparity difference) and with respect to the bent angle in degrees (viewing direction). The measurement of the reaction times allows a numerical quantification of the degree to which the fusion capacity is limited, depending on the viewing direction and as a function of the difference in disparity.

The method according to the invention makes it possible to generate a two-dimensional visual field mapping from the measurements of the reaction time at the respective degree of difficulty S in arcsec and the respective bent angle $\beta$, which allows a very clear overview of the quality of the fusion capacity in conjugate eye movements of a subject as a function of viewing direction.

For the same subject, the measurements are expediently carried out repeatedly in at least one, preferably a plurality of later time points, as a result of which comparison measurements or comparison visual field mappings are obtained from different times. In turn, the acute defect or the healing process of the person concerned can be visually documented.

Conveniently, the visual stimulus for stereopsis can be generated virtually, in particular by using a so-called VR (virtual reality) headset or a head-mounted display.

The invention further relates to a device for quantitatively detecting the fusion capacity in conjugate eye movements of a subject, comprising a device for generating and presenting a stimulus for stereopsis as an individual stimulus as a task for the subject, the stimulus being generated at an angle $\alpha$ relative to the primary viewing direction of the subject in such a way that the subject has to perform a movement of the viewing direction of the eyes away from the primary viewing direction, and wherein the stimulus is generated successively at different bent angles $\beta$ of the visual field range, a time-recording device with which the respective reaction time to the stimulus is detected at different cognitive degrees of difficulty at the different bent angles $\beta$, and an input device for triggering the time recording device, the input device being actuated by the subject, preferably manually or acoustically, and a control and evaluation module.

Within the scope of the device, a VR headset is preferably provided as a device for generating and presenting a stimulus for stereopsis.

The data obtained by means of the method according to the invention are suitable for being visualized, digitized or digitally processed and/or systematized in databases.

DESCRIPTION OF THE INVENTION WITH REFERENCE TO EXEMPLARY EMBODIMENTS

Figure 2:
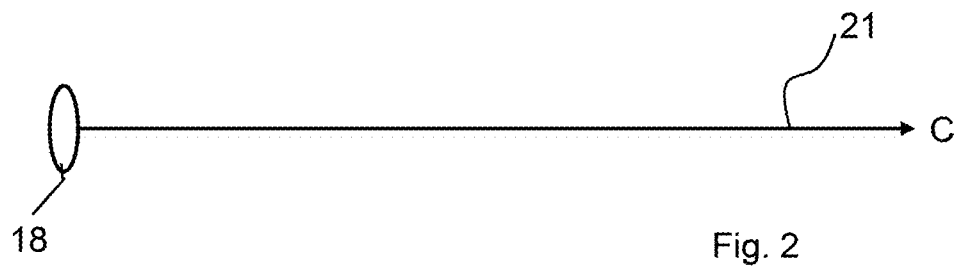
Figure 3:
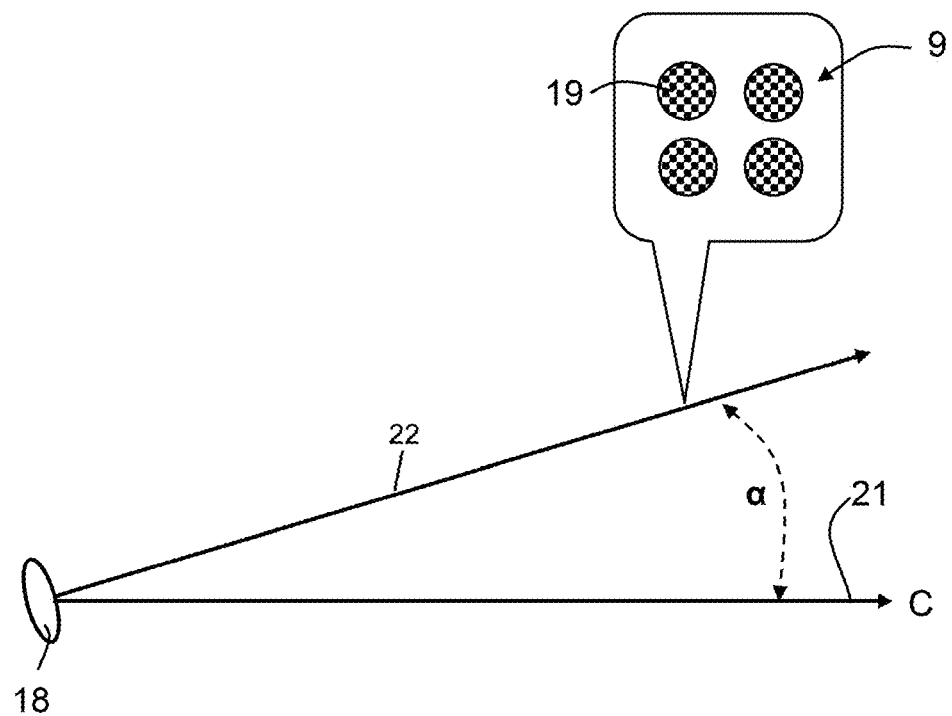
Figure 4:
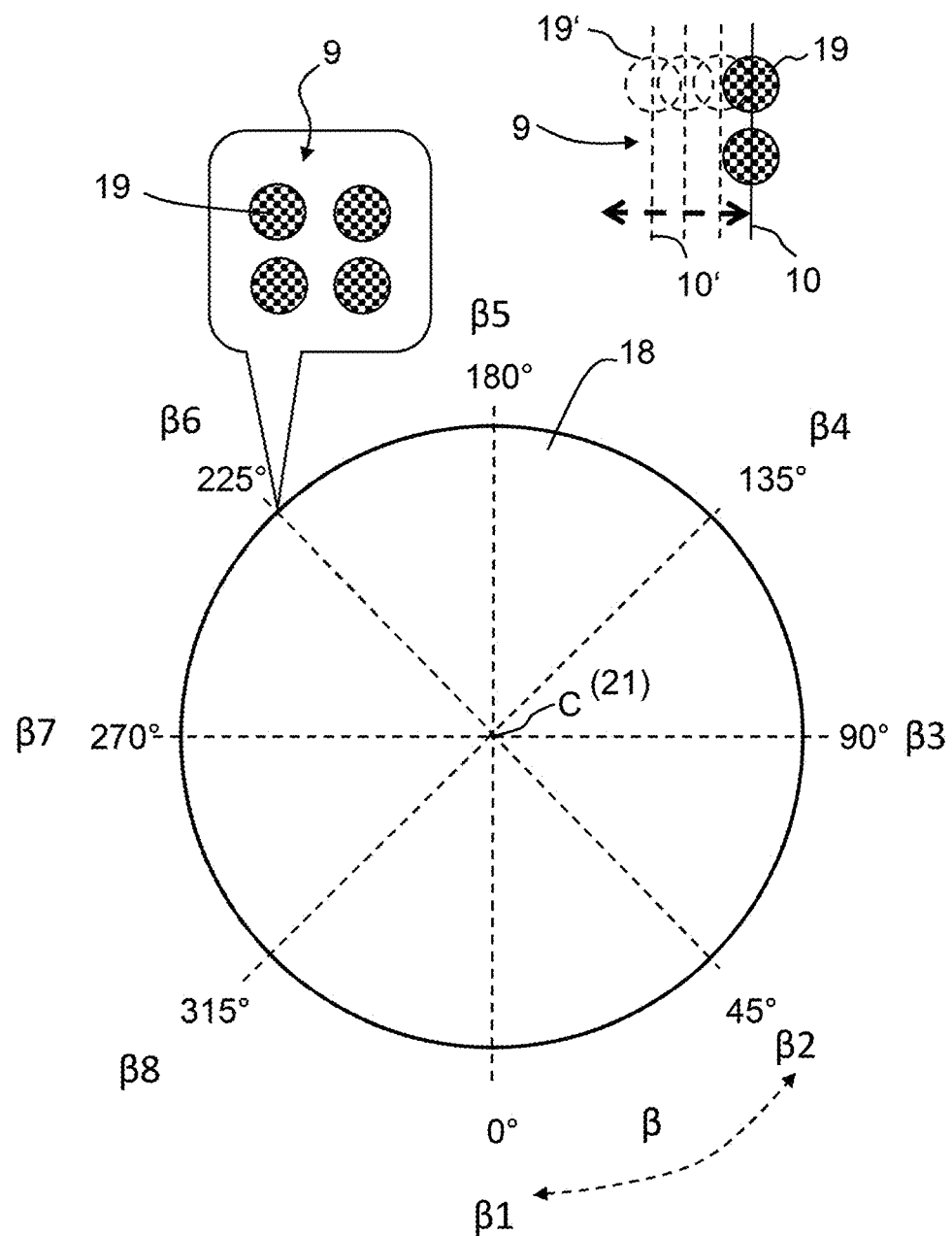
Figure 5:
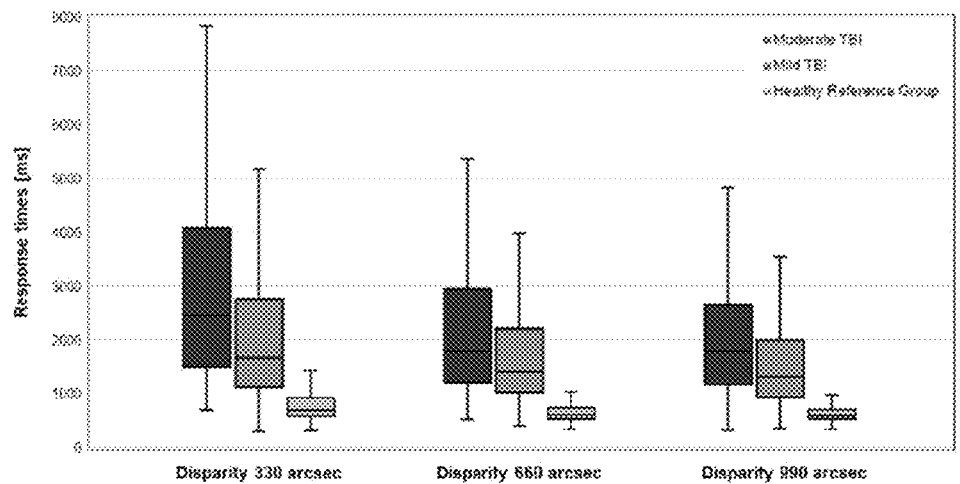
Figure 6:
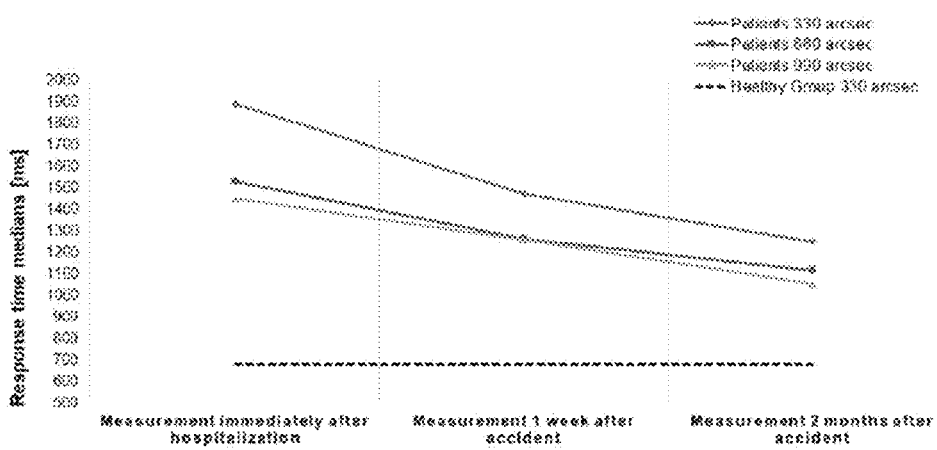
Figure 7:
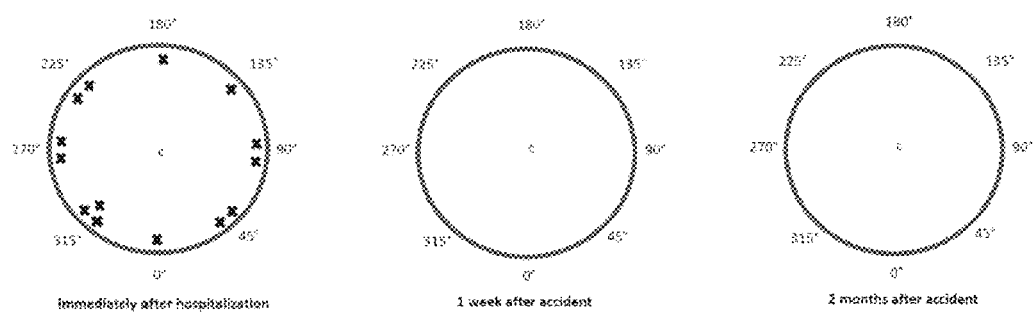
Figure 8:
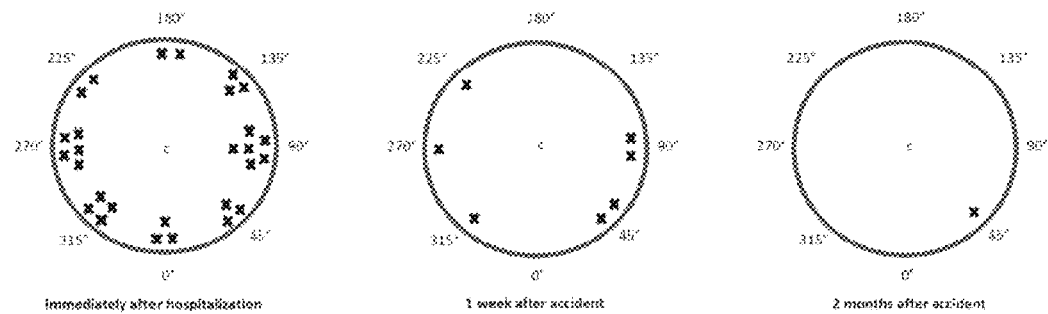
Figure 9A:
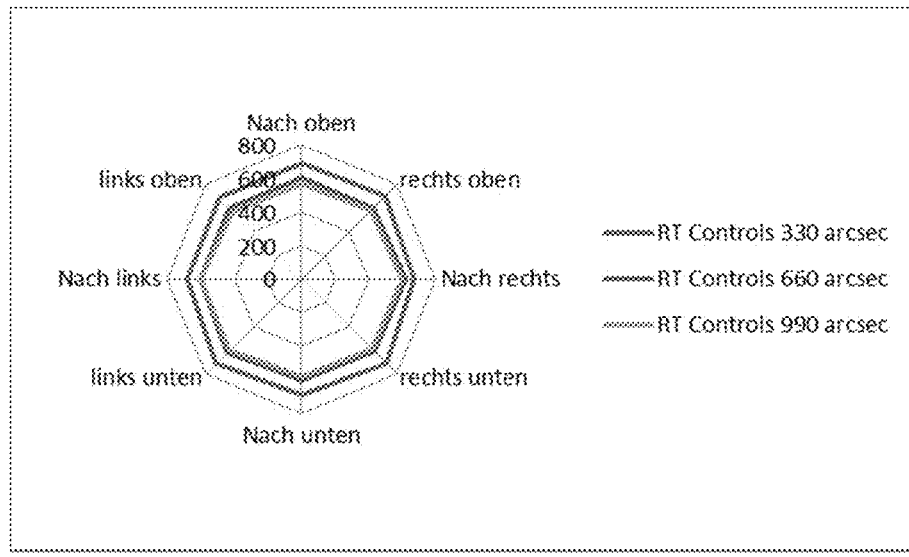
Figure 9B:
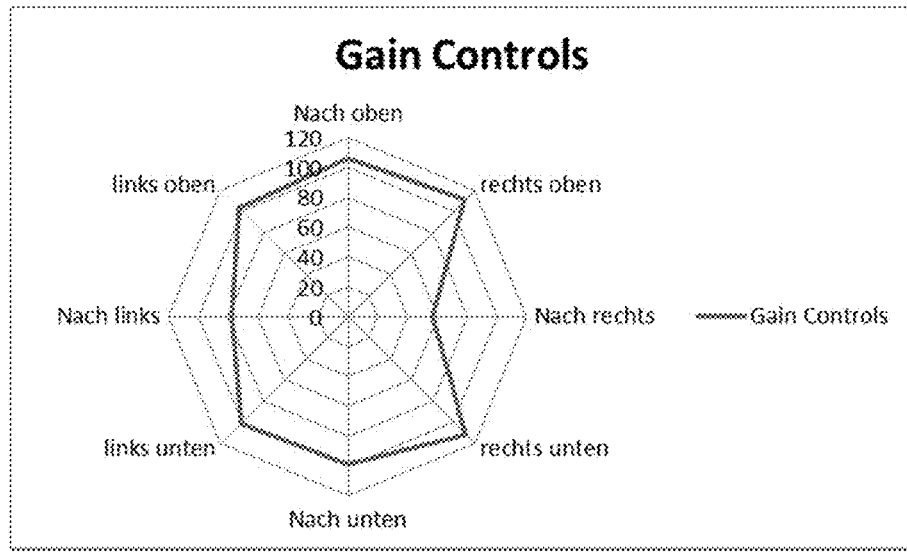
Figure 10A:
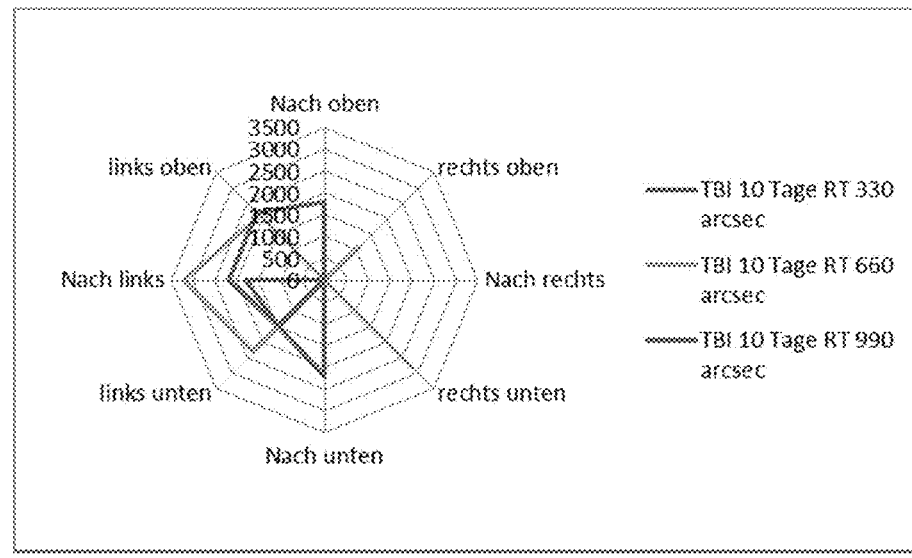
Figure 10B:
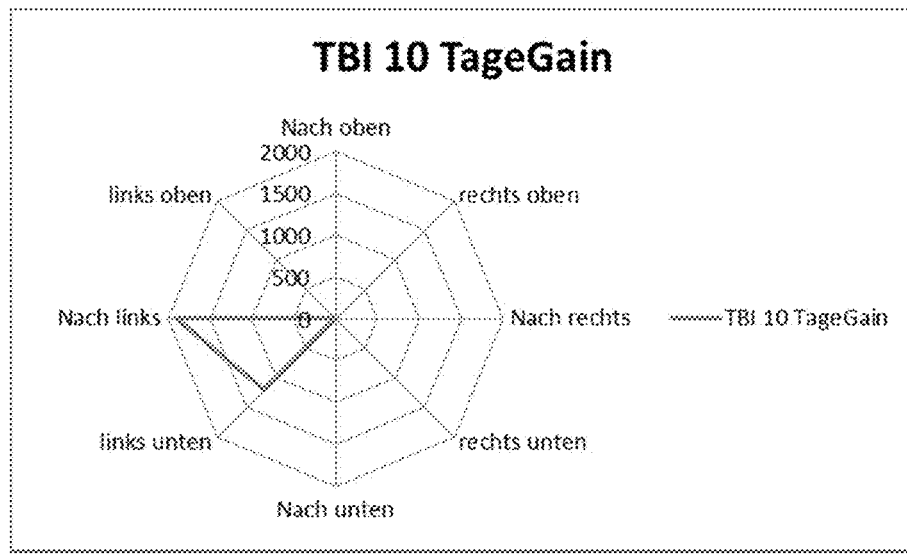
Figure 10C:
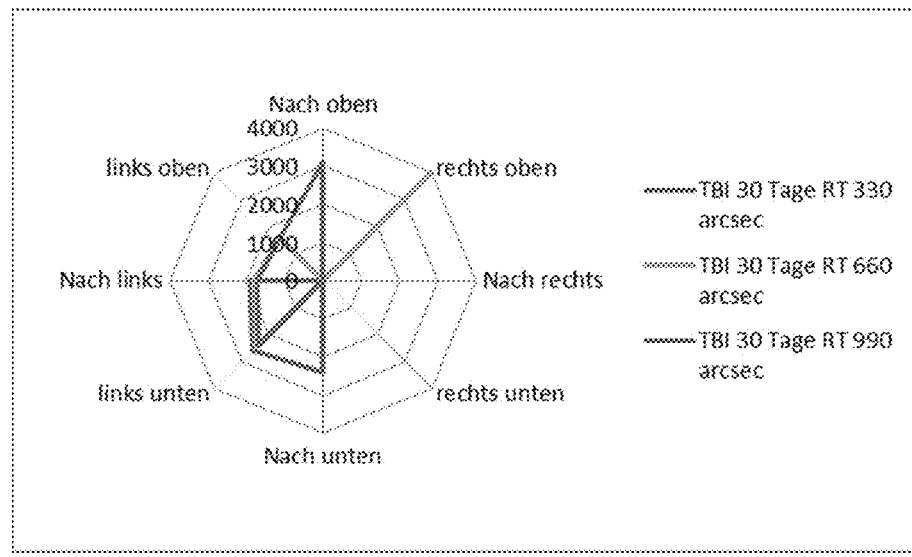
Figure 10D:
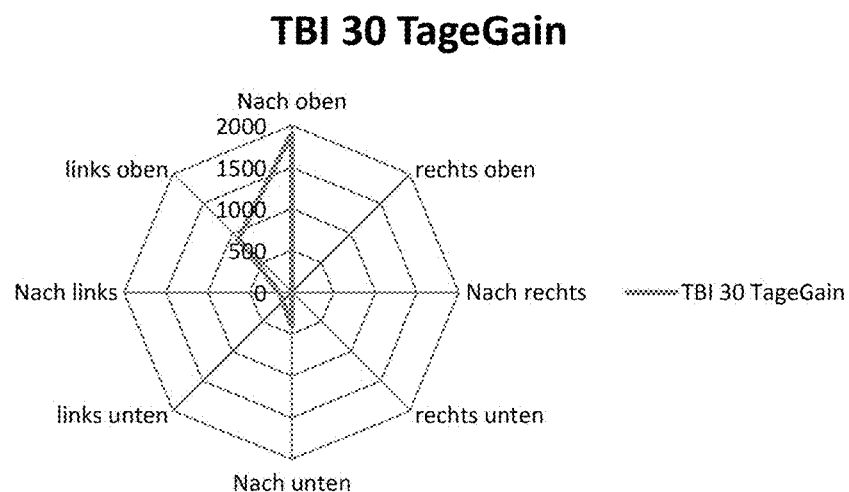
Figure 10E:
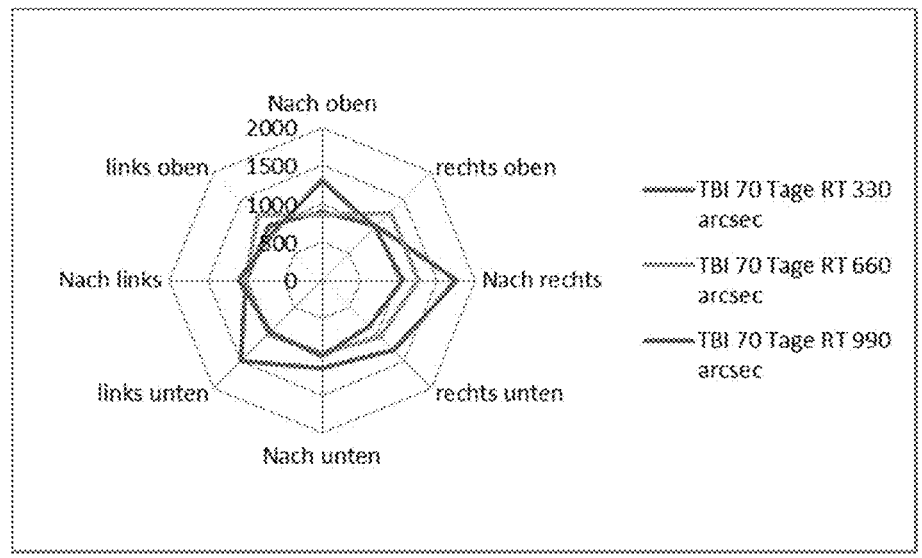
Figure 10F:
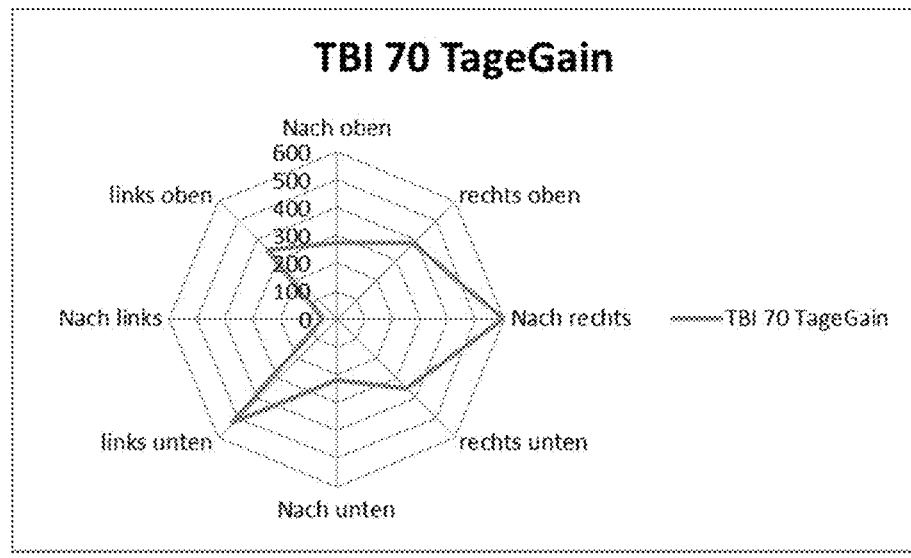

Advantageous embodiments of the present invention will be explained in more detail with reference to the drawing figures. Recurring features are identified only once with a reference numeral for the sake of clarity. Shown are:

FIG. 1 a greatly simplified schematic representation of a device for carrying out the method according to the invention;

FIG. 2 a greatly simplified schematic representation of the primary viewing direction;

FIG. 3 a greatly simplified schematic representation of a stimulus for disparity in a viewing angle α relative to the primary viewing direction according to a further example of the method according to the invention;

FIG. 4 a greatly simplified schematic representation of a stimulus for disparity at different arc angle β dimensions of the field of vision range in accordance with a further example of the method according to the invention;

FIG. 5 mean values of the reaction times of all viewing directions with stimuli at 330, 660 and 990 arcsec of disparity difference for healthy subjects as well as subjects with mild or moderate concussion;

FIG. 6 an illustration of the plot of the mean values of the reaction times of all viewing directions over several weeks at stimuli of 330, 660 and 990 arcsec of disparity difference for healthy subjects as well as subjects with mild or moderate concussion;

FIG. 7 a representation of the positions of viewing directions determined by the method according to the invention where there is no ability to fuse as a function of different bent angle positions in the visual field of subjects with mild concussion immediately after admission to the clinic, one week after the accident and two months after the accident;

FIG. 8 a representation of the positions of deficits in the ability to merge, determined by the method according to the invention, as a function of viewing directions with no fusion capacity relative to subjects with moderate concussion immediately after hospital admission, one week after the accident and two months after the accident;

FIG. 9a-9b graphical representations (viewing direction mapping) of the reaction times in msec of healthy subjects (called controls here) as a function of different bent angle positions in the visual field at different levels of difficulty S (FIG. 9a) and a graphical representation (visual field mapping) of the increase in response time in milliseconds with increasing difficulty of the stereoscopic stimulus ("gain") in healthy subjects ("gain controls") from the measurements of FIG. 9a; and FIG. 10a-10f representations of the development of a concussion over a period of 70 days from a subject with mild TBI, using graphical representations (visual field mapping) of the reaction times as a function of different bent angle positions in the visual field at different levels of difficulty S, and the respective associated graphical representation of the increase in reaction time in msec with increasing degree of difficulty (gain) at 10 days after concussion (FIGS. 10a and 10b), at 30 days after concussion (FIGS. 10c and 10d) and at 70 days after concussion (FIG. 10e and FIG. 10f).

FIG. 1 shows an example of a device for the quantitative acquisition of measurements in connection with fusion capacity in conjugate eye movements of a subject P. The device 1 comprises an imaging module 2, which serves to generate a disparity difference stimulus 9 at a viewing angle α which lies outside the primary viewing direction 21. The stimulus 9 is shown in FIG. 1 viewed from the side. In the present case, for example, a stimulus 9 acting three-dimensionally on the subject P is generated in a monitor 7 or display 6 in the form of four objects 19 in the form of balls lying in the optical plane 10. In this case, one ball is shown with a certain disparity difference from the other 3 balls, that is to say with respect to the position of its optical plane relative to the optical plane of the three other balls. The stimulus 9 is used to determine the fusion capacity, in conjugate eye movements, of for example stereoscopic images which are outside the primary viewing direction, i.e. in a visual field in which the muscles which control eye movement are stressed or tense.

The stimulus is set at different degrees of difficulty S, i.e. at a different disparity difference relative to the main virtual plane. For this purpose, one object 19' of the four objects 19 is represented with a certain disparity difference, that is to say it is shown in a different optical plane 10' relative to the optical plane 10 of the other three objects 19. The degree of disparity difference, i.e. the distance between optical plane 10' and optical plane 10 in FIG. 1 represents the degree of difficulty of the disparity difference of the stimulus. The farther the distance between the main virtual plane and the plane of the different object, the lower the degree of difficulty (the easier it is to detect the difference in disparity of the subject); the closer the optical plane 10' comes to the optical plane 10 the higher the level of difficulty (the more difficult it is to detect the difference in disparity for the subject). The difficulty level is set in the units of arcsec in the system.

The subject P can be equipped for this purpose with a VR (VR=Virtual Reality) headset 8 in which two images which are different for the right and left eyes, respectively, are generated by a computer program such that in binocular viewing by the subject P's brain the images are seen as the only stereoscopic image in the display 6 of the VR headset 8. According to FIG. 3, the stimulus 9 using the four objects 19, wherein one object has a difference in disparity, is presented to the subject P successively with different differences in disparity and thus in different virtual optical planes 10'. When the subject P recognizes one ball of the four balls that has a difference in disparity, it triggers a corresponding reaction, from which the reaction time is measured from the time the stimulus 9 is given to the time the reaction is triggered. For example, the subject presses the button of a four-button manual input 11 (e.g. a touchpad) which represents the ball in question.

If the subject actuates the manual input 11, for example a push-button or a touchpad, the reaction time from the presentation of the stimulus 9 to the actuation of the manual input device 11 is measured by a time-recording device 3 and fed to a control and evaluation module 4 and is assigned to the respective level of difficulty in arcsec. Thereafter, the test is continued with a stimulus 9 in the form of four objects 19, wherein the same or another of the four objects 19 is shown at a different disparity difference, i.e. at a different degree of difficulty S, and thus in a different optical plane 10'. The control and evaluation module 4 can have an output 5 (e.g. to a printer) as well as a monitor 7 for displaying the measurements. Furthermore, the control and evaluation module 4 expediently comprises a storage device 17. The visual stimuli 9 of different degrees of difficulty are shown in dashed lines in FIG. 1.

The illustration according to FIG. 2 shows the primary viewing direction 21 of a person. The primary viewing direction 21 corresponds to the center C of the visual field. In the primary viewing direction 21, the muscles controlling the eye movement need not be stressed or strained. The primary direction of vision 21 has no significance regarding the evaluation of a concussion. For this reason, a stimulus 9 for disparity is given in a viewing area outside the primary viewing direction 21, i.e. in a viewing area in which the muscles controlling the eye movement actually have to be stressed. Such a viewing direction is indicated in FIG. 3 by the reference numeral 22 and lies in an angle α relative to the primary viewing direction 21. The stimulus 9 is generated in this viewing direction 22 according to the method according to the invention.

The graph of FIG. 5 shows disparity measurements of varying degrees of difficulty (330 arcsec, 660 arcsec and 990 arcsec) of three different subject groups, healthy subjects, mild TBI subjects and moderate TBI subjects. For this purpose, the disparity investigations were carried out in different viewing directions α relative to the primary viewing direction and averaged over all measured primary viewing directions. FIG. 5 shows that the mean response times are significantly prolonged in patients with mild and moderate concussion. The method according to the invention thus makes it possible to detect a slight concussion (mild TBI) compared to a healthy person without concussion.

Furthermore, it is also possible by means of the method according to the invention to test a subject as to whether the subject has suffered a mild concussion (mild TBI) or a moderate concussion (moderate TBI). As a result, appropriate measures can be initiated. For example, when a moderate concussion (moderate TBI) is determined, an athlete may be excluded from exercise for a prolonged period of time.

FIG. 6 shows a monitoring of the development of a concussion using the method according to the invention. For this purpose, the fusion capacity of the conjugate eye movements of all subjects with moderate or mild concussion (moderate and mild TBI) at various times were plotted versus time at T1 (detection immediately after admission), T2 (detection one week after the accident) and T3 (detection two months after the accident). FIG. 6 shows that the mean reaction times in patients with mild and moderate concussion normalize over time, but even after 70 days do not reach the values of healthy control persons.

According to a further embodiment of the method according to the invention, in a viewing direction 22, the visual field range 18 can be divided into specific, fixed bent angle positions β. For example, in the example shown in FIG. 4, a total of eight bent angle positions β1-β8 are set. These are the bent angle positions 0°, 45°, 90°, 135°, 180°, 225°, 270° and 315°. At each of these fixed bent angle positions, a disparity stimulus 9 of varying difficulty S is issued. In FIG. 4, for the sake of illustration, a stimulus 9 has been drawn in at a bent angle of β6 (225°). The respective bent angle positions β1-β8 are preset in the control and evaluation module 4, presented accordingly to the subject by the VR headset 8 and assigned to the reaction time measurements and levels of difficulty.

The control and evaluation module 4 expediently comprises a random-number generator or pseudo-random generator 13, which ensures that the individual stimuli 9 of different degrees of difficulty S and the respective bent angle positions β are randomly presented to the subject P. This prevents cognitive learning effects from falsifying the measurement result.

An evaluation of the fusion capacity in conjugate eye movements as a function of the respective bent angle position β is shown in FIG. 7 for patients with mild concussion and in FIG. 8 for patients with moderate concussion, on the one hand immediately after their admission, one week after the accident as well as two months after the accident. As is clear from FIG. 7, in persons with mild concussion there is no further impairment of the visual field with respect to the fusion capacity in conjugate eye movements after one week.

In contrast, the fusion capability in persons with moderate concussion as shown in FIG. 8 is noticeably disturbed even after a week, especially with regard to viewing to the right and left. In addition, it can be seen from FIG. 8 that the impairment of the fusion capacity immediately after the accident is particularly high with regard to viewing to the left and to the right.

FIGS. 7 and 8 clearly show that the method according to the invention can enable a quantitative assessment of the fusion capacity in conjugate eye movements of a subject to be made, the results of which can be used for the assessment of the degree of severity of the concussion. The method according to the invention thus makes it possible to carry out a relevant differentiation with comparatively simple means.

Tab. 1 shows corresponding measurements of the reaction times in msec of a healthy person. For this purpose, conjugate eye movement measurements were made on a select group of healthy persons at different bent angle positions β (0° "down," 45° "down and right," 90° "to the right," 135° "up and right," 180° "up," 225° "up and left," 270° "to the left," 315° "down and left" at stimuli 9 with different difficulty levels S (330, 660 and 990 arcsec). "Gain Controls" refers to the increase in response time with increasing difficulty S in healthy individuals. The gain was calculated for every angle.

TABLE 1

| Viewing direction | β | RT Controls 330 arcsec | RT Controls 660 arcsec | RT Controls 990 arcsec | Gain Controls [msec/ 330 arcsec] |
|---|---|---|---|---|---|
| Up | 180 | 692 | 603 | 569 | 106 |
| Up and right | 135 | 703 | 603 | 581 | 111 |
| To the right | 90 | 670 | 625 | 603 | 56 |
| Down and right | 45 | 715 | 615 | 592.5 | 111.25 |
| Down | 0 | 690 | 602 | 580 | 99 |
| Down and left | 315 | 715 | 625 | 603 | 101 |
| To the left | 270 | 680.5 | 603 | 603 | 77.5 |
| Up and left | 225 | 692 | 603 | 574.5 | 103.25 |

FIG. 9a shows a corresponding two-dimensional visual field mapping of healthy persons based on the measurements. With a corresponding visual field mapping, an effective means is provided which allows the examining doctor to recognize at a glance the state of the fusion capacity in the conjugate eye movements of a subject.

FIG. 9b is a graphical representation of the increase in response time in msec as the degree of difficulty of the stereoscopic stimulus (gain) increases in healthy subjects ("gain controls") for the measurements of FIG. 9a. There is an increase in response time in a range of 60-100 msec as the degree of difficulty increases from 990 arcsec of disparity difference to 660 arcsec of disparity difference and from 660 arcsec to 330 arcsec of disparity difference, respectively.

Tab. 2 shows corresponding measurements of the reaction times in msec of a person 10 days after having suffered a concussion (TBI 10 days after). "x" means that the subject did not achieve fusion of the images of both eyes at this viewing angle and did not detect a disparity difference.

"#VALUE!" in the table means that there was no fusion in these measured viewing directions and therefore no gain value could be given.

TABLE 2

| Viewing direction in the diagram | Viewing direction β | Reaction time 330 | Reaction time 660 | Reaction time 990 | GAIN [msec/ 330 arcsec] |
|---|---|---|---|---|---|
| Up | 180 | x | x | 1800 | #VALUE! |
| Up and right | 135 | x | 1100 | x | #VALUE! |
| To the right | 90 | x | x | x | #VALUE! |
| Down and right | 45 | x | 2800 | x | #VALUE! |
| Down | 0 | 2200 | x | x | #VALUE! |
| Down and left | 315 | 1500 | 2300 | 1500 | 1200 |
| To the left | 270 | 1800 | 3200 | 2200 | 1900 |
| Up and left | 225 | x | 2100 | 2200 | #VALUE! |

FIG. 10a shows a corresponding two-dimensional visual field mapping based on the above measurements. The illustration shows that 10 days after the concussion, conjugate eye movement in the viewing directions to the right, up and right, up and down, and thus a fusion of the image impressions of the right and left eyes is difficult or impossible.

FIG. 10b shows the increase in reaction time in msec only in viewing directions with existing fusion as the degree of difficulty of the stereoscopic stimulus increases (gain). 10 days after the concussion, the reaction time increase was ca. 1000 msec with an increase of the degree of difficulty from 990 arcsec of disparity difference to 660 arcsec of disparity difference and from 660 arcsec to 330 arcsec of disparity difference and thus a factor of 10 higher than in healthy persons.

Thus, in this subject, the plot of reaction times and gain at 10 days post-concussion reveals a complete lack of fusion in conjugate eye movement to the right, markedly longer reaction times to the left and significantly increased reaction times (gain) for increasingly difficult stereoscopic stimuli.

Tab. 3 shows corresponding measurements of the reaction times in msec of a person 30 days after the concussion is suffered (TBI 30 days after). "x" means that the subject did not fuse the images of both eyes at this viewing angle and did not detect a disparity difference.

"#VALUE!" in the table means that there was no fusion in these measured viewing directions and therefore no gain value could be given.

TABLE 3

| Viewing direction in the diagram | Viewing direction β | Reaction time 330 | Reaction time 660 | Reaction time 990 | GAIN [msec/ 330 arcsec] |
|---|---|---|---|---|---|
| Up | 180 | x | x | 3100 | 1900 |
| Up and right | 135 | x | 4000 | x | #VALUE! |
| To the right | 90 | x | x | x | #VALUE! |
| Down and right | 45 | x | x | x | #VALUE! |
| Down | 0 | 2400 | x | x | 400 |
| Down and left | 315 | 2600 | 2500 | 2400 | 150 |
| To the left | 270 | 1900 | 1800 | 1700 | 150 |
| Up and left | 225 | x | 1600 | 1600 | 900 |

FIG. 10c shows a corresponding two-dimensional visual field mapping based on the above measurements. The illustration shows that 30 days after the concussion, conjugated eye movements to the right, up and right, up and down are still difficult or impossible.

FIG. 10d shows the increase in reaction time in msec only in viewing directions with existing fusion and increasing degree of difficulty of the stereoscopic stimulus (gain). At 30 days post-concussion, the reaction time increase was still significantly increased from 150 to 1900 msec/330 arcsec as the degree of difficulty increased from 990 arcsec of disparity difference to 660 arcsec of disparity difference, and from 660 arcsec to 330 arcsec of disparity difference.

Tab. 4 shows corresponding measurements of the reaction times in msec of a person 70 days after suffering a concussion (TBI 70 days after).

TABLE 4

| Viewing direction in the diagram | Viewing direction β | Reaction time 330 | Reaction time 660 | Reaction time 990 | GAIN [msec/ 330 arcsec] |
|---|---|---|---|---|---|
| Up | 180 | 900 | 850 | 1300 | 275 |
| Up and right | 135 | 1000 | 1250 | 980 | 385 |
| To the right | 90 | 1750 | 1250 | 1050 | 600 |
| Down and right | 45 | 1300 | 1050 | 850 | 350 |
| Down | 0 | 1150 | 950 | 990 | 220 |
| Down and left | 315 | 1500 | 1000 | 950 | 525 |
| To the left | 270 | 1000 | 1000 | 1100 | 50 |
| Up and left | 225 | 1000 | 1200 | 900 | 350 |

FIG. 10e shows a corresponding two-dimensional visual field mapping based on the above measurements. The illustration shows that 70 days after the concussion, there is now proper fusion in the direction of view to the right, but the reaction times are still longer.

FIG. 10f shows the increase in reaction time in msec now in all directions with existing fusion and increasing degree of difficulty of the stereoscopic stimulus (gain). At 70 days post-concussion, the reaction time increase was still prolonged from 275 to 600 msec/330 arcsec as the degree of difficulty increased from 990 arcsec of disparity difference to 660 arcsec of disparity difference and from 660 arcsec to 330 arcsec of disparity difference, respectively.

After 70 days, there was thus a marked improvement in stereoscopic vision, but not yet a complete normalization, as the comparison with the healthy subjects (FIG. 9) shows.

In summary, it should therefore be stated that with the method according to the invention or the device according to the invention, the severity of a concussion can be determined in the context of a rapid test and measures can be taken effectively in view of avoiding long-term damage in the case of a concussion. This is of particular importance for those at risk, such as athletes or military personnel. The device for carrying out the method according to the invention can also be used as a portable test device on site, e.g. at sports fields, in the field and the like.

Alternatively or additionally, the measurement results or derived data can also be output via a data output 12, for example an interface, to other users who are connected by means of a cable connection 20/wireless connection 20, e.g. to a modem 14. If necessary, the data can be supplied via the modem 14, a network or the Internet 15 and stored centrally from there, for example in a computer cloud 16.

The setting of the viewing angle α is preferably in a range of at least 10° to a maximum of 45°, preferably a maximum of 40°. This range is sufficient for carrying out the measurements against the background of stress on the nerves controlling the eye muscles and is also technically possible in connection with the use of a VR headset.

LIST OF REFERENCE SIGNS

1 Device
2 Imaging module
3 Time recording device
4 Control and evaluation module 5 Output
6 Display
7 Monitor
8 VR headset
9 Stimulus
10 Optical plane
11 Manual input
12 Data output
13 Random generator
14 Modem
15 Internet
16 Computer cloud
17 Memory
18 Visual field range
19 Object
20 Cable connection/wireless connection
21 Primary viewing direction
22 Viewing direction
P Subject
S Degree of difficulty
T Reaction time

The invention claimed is:

1. A method for quantitatively detecting the fusion capacity in conjugate eye movements of a subject, comprising the following process steps:
    (a) providing visual stimuli for stereopsis as a task for the subject, the stimuli being generated at a viewing angle relative to a primary viewing direction of the subject such that the subject must execute a movement of a viewing direction of eyes of the subject away from the primary viewing direction,
    (b) presenting each stimulus for a given period of time so that the subject can perceive the respective stimulus,
    (c) the subject reacting to the respective stimulus perceived thereby within a reaction time, triggering a motor reaction to be detected,
    (d) determining the reaction time as a time between the presentation of the respective stimulus and the detected motor reaction of the subject as a result of the stimulus,
    wherein steps (a) to (d) are carried out continuously with the stimuli for stereopsis at a varying cognitive degree of difficulty for the subject,
    wherein a series of measurements in the form of reaction times at different cognitive degrees of difficulties is generated,
    wherein the stimuli for stereopsis are generated in bent angle positions at a different cognitive degree of difficulty, and
    a respective reaction time to the stimuli is detected.

2. The method according to claim 1, wherein the bent angle positions have a same bent angle separation from each other.

3. The method according to claim 1, wherein the measured reaction times are compared with target reaction times.

4. The method according to claim 3, wherein the target reaction times are reaction times of healthy persons.

5. The method according to claim 1, wherein the stimuli for stereopsis include at least two images of an object or stochastically generated stereo images which are presented to the subject in optical planes at different distances to the subject.

6. The method according to claim 1, wherein the respective stimuli are an image of a plurality of fixed objects or objects rotating about the axes thereof, one of which having changed in a remote optical plane thereof compared to the optical plane of the other objects as a function of the degree of difficulty.

7. The method according to claim 1, wherein the viewing angle is at least 10°.

8. A method according to claim 1, wherein the viewing angle is a maximum of 45°.

9. The method according to claim 1, wherein an increase in reaction time with increasing degree of difficulty is determined.

10. The method according to claim 1, wherein an assignment of the measurements of the reaction time is done in assignment to the degree of difficulty and to the bent angle.

11. The method according to claim 1, wherein a two-dimensional visual field mapping is generated from the measurements of the response time at the respective degree of difficulty and the respective bend angle.

12. The method according to claim 1, wherein comparison measurements are repeated at a later time for the same subject.

13. The method according to claim 1, wherein the stimuli are generated by a random generator or pseudo-random generator.

14. The method according to claim 1, wherein the visual stimulus for stereopsis is generated virtually, by a virtual reality (VR) headset.

15. A device for quantitatively determining fusion capacity in conjugate eye movements of a subject, comprising:
    a device for generating and presenting a stimulus for stereopsis as an individual stimulus as a task for the subject, wherein the stimulus is generated in an angle relative to a primary viewing direction of the subject, so that the subject has to perform a movement of a viewing direction of eyes of the subject away from the primary viewing direction,
    a timer for detecting a respective reaction time to the stimulus at different cognitive degrees of difficulty,
    an input device for triggering the timer operable by the subject, and
    processor, which generates a series of measurements of reaction times at different cognitive degrees of difficulty by generating stimuli for stereopsis in bent angle positions at a different cognitive degree of difficulty and detecting the respective reaction time to the stimuli.

16. The device according to claim 15, wherein a virtual reality headset or a head-mounted display is provided for generating and presenting a stimulus for stereopsis.

* * * * *